US007927560B2

(12) United States Patent
Richard

(10) Patent No.: US 7,927,560 B2
(45) Date of Patent: Apr. 19, 2011

(54) SPECIMEN CUP SYSTEM FOR SAMPLE TESTING AND SECURE RETENTION

(75) Inventor: M. Nee Richard, Virginia Beach, VA (US)

(73) Assignee: Bio Screens Inc., Norfolk, VA (US)

( * ) Notice: Subject to any disclaimer, the term of this patent is extended or adjusted under 35 U.S.C. 154(b) by 233 days.

(21) Appl. No.: 12/381,722

(22) Filed: Mar. 16, 2009

(65) Prior Publication Data

US 2009/0232709 A1 Sep. 17, 2009

Related U.S. Application Data

(60) Provisional application No. 61/069,722, filed on Mar. 17, 2008.

(51) Int. Cl.
*G01N 33/00* (2006.01)

(52) U.S. Cl. ........ 422/401; 422/400; 422/402; 422/408; 422/420; 422/68.1

(58) Field of Classification Search .................. 422/400, 422/401, 402, 406, 420, 68.1
See application file for complete search history.

(56) References Cited

U.S. PATENT DOCUMENTS

| | | | | |
|---|---|---|---|---|
| 6,277,646 | B1 * | 8/2001 | Guirguis et al. | 436/165 |
| 6,576,193 | B1 | 6/2003 | Cui et al. | |
| 2003/0022392 | A1 * | 1/2003 | Hudak | 436/518 |
| 2003/0027359 | A1 * | 2/2003 | Hudak et al. | 436/518 |
| 2003/0099572 | A1 * | 5/2003 | Ng et al. | 422/58 |
| 2006/0029517 | A1 * | 2/2006 | Hartselle | 422/61 |

* cited by examiner

*Primary Examiner* — Sam P Siefke
(74) *Attorney, Agent, or Firm* — Peter J. Van Bergen

(57) ABSTRACT

A specimen cup system for sample testing includes a cup defining sealable first and second regions. A receptacle is formed at a bottom of the first region and extends vertically therein. The receptacle has a first opening defined at the bottom of the first region, a second opening in a radial wall of the receptacle for fluid communication with the first region, and a third opening in the radial wall of the receptacle for fluid communication with the second region. A base having a hollow post is inserted in the first opening of the receptacle. The hollow post has a radial opening formed therein that, when aligned with the second opening, defines a pre-test condition. The hollow post forms a fluid tight seal with the receptacle about the radial opening. The base is coupled to the bottom of the cup in a rotatable fashion such that the hollow post can be rotated to align the radial opening thereof with the third opening in the receptacle to define a test condition. At this point, the base is locked to the cup to prevent further relative rotation therebetween.

20 Claims, 9 Drawing Sheets

SPECIMEN CUP SYSTEM FOR SAMPLE TESTING AND SECURE RETENTION

ORIGIN OF THE INVENTION

Pursuant to 35 U.S.C. §119, the benefit of priority from provisional application 61/069,722, with a filing date of Mar. 17, 2008, is claimed for this non-provisional application.

FIELD OF THE INVENTION

The invention relates generally to testing of body-fluid samples, and more particularly to a specimen cup system that provides for sample testing and secure retention of a portion of the sample in a tamper-resistant container that keeps the sample free of contaminants.

BACKGROUND OF THE INVENTION

Body-fluid-based drug testing has become pervasive in our modern society. From government and industry workers to amateur and professional athletes, most people will be subject to at least one drug test at some point in their life. Accordingly, it is imperative that the drug testing industry provide drug testing systems that guarantee that a body-fluid sample will remain contaminant-free before, during and after a drug test.

By and large, drug testing "systems" utilize some type of specimen cup that a user fills or partially fills with a body-fluid sample. Recently, a variety of specimen cups have included the means to have a drug test card inserted therein where the card is exposed to the body-fluid sample and subsequently provides an indication about the presence/absence of one or more substances of interest. However, to date, no drug testing specimen cup exists that provides for collection of a body-fluid sample, testing of a portion of the sample, and the guaranteed secure retention of the remainder of the sample in a tamper-resistant and contaminant-free environment. This is critical if re-testing of the sample is required. That is, if the results of a drug test are in question and the drug-testing system has not retained some of the sample is a secure fashion for later confirmation testing, the subsequent "confirmation test" will also be called into question.

SUMMARY OF THE INVENTION

Accordingly, it is an object of the present invention to provide a specimen cup system for drug testing.

Another object of the present invention is to provide a specimen cup system that can be used to collect a body-fluid sample and test a portion of the sample while retaining a remainder of the sample in a tamper-resistant and contaminant-free environment.

Other objects and advantages of the present invention will become more obvious hereinafter in the specification and drawings.

In accordance with the present invention, a specimen cup system for sample testing includes a cup defining a first region and a second region adjacent to the first region. A receptacle is formed at a bottom of the first region and extends vertically therein. The receptacle has (i) a first opening defined at the bottom of the first region, (ii) a second opening in a radial wall of the receptacle for fluid communication with the first region, and (iii) a third opening in the radial wall of the receptacle for fluid communication with the second region. A base having a hollow post extending vertically therefrom is inserted in the first opening of the receptacle. The hollow post has a radial opening formed therein that, when aligned with the second opening, defines a pre-test condition. The hollow post further forms a fluid tight seal with the receptacle about the radial opening. The base is coupled to the bottom of the cup in a rotatable fashion such that the hollow post can be rotated to align the radial opening thereof with the third opening in the receptacle to define a test condition. At this point, the base is locked to the cup to prevent further relative rotation therebetween. A first top seals the first region, and a second top seals the second region. A specimen test card can be placed in the second region to test fluid introduced therein during a test condition.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
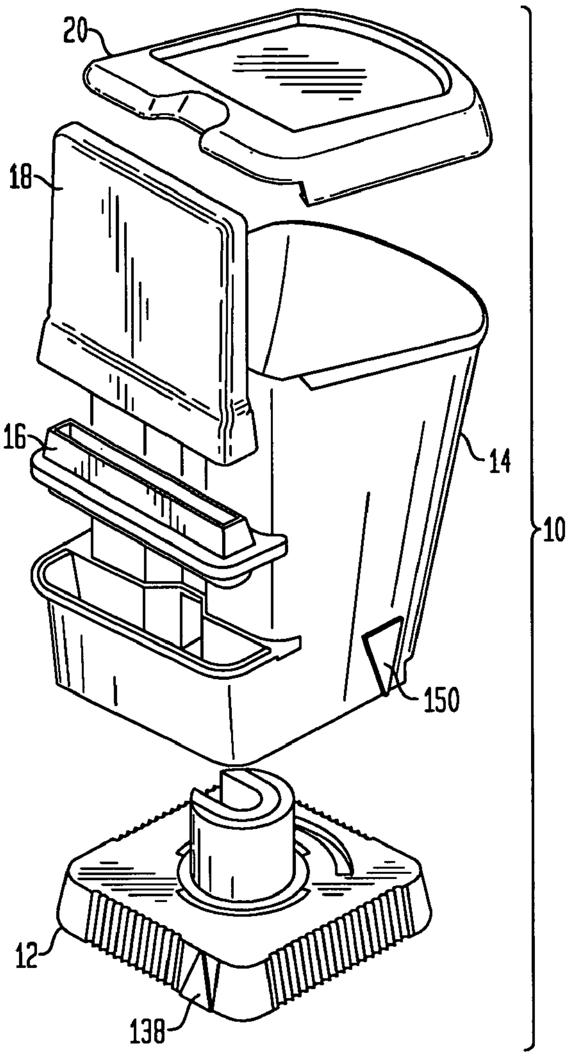
FIG. 1 is an exploded perspective view of a specimen cup system in accordance with an embodiment of the present invention with the system in its pre-test position.
Figure 2:
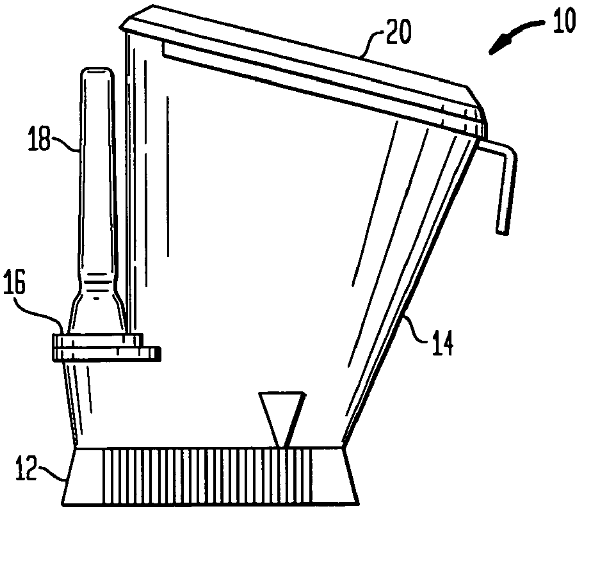
FIG. 2 is a side view of an assembled specimen cup system in its pre-test position.

Referring now to the drawings and more particularly to FIGS. 1 and 2, a specimen cup system in accordance with an embodiment of the present invention is shown and is referenced generally by numeral 10. In general, specimen cup system 10 can be used to collect, test, and retain body-fluids (e.g., urine, blood, saliva, semen, etc.) deposited therein. As will be explained further herein, specimen cup system 10 seals the body-fluid therein prior to the testing thereof, provides for in-situ and on-demand drug testing of a portion of the body-fluid, and securely retains a remainder of the body-fluid in a tamper-resistant and contaminant-free environment.

The illustrated embodiment of specimen cup system 10 possesses several novel features that can be implemented in other ways than shown and described herein without departing from the scope of the present invention. Accordingly, it is to be understood that the novel aspects of the present invention are not limited by the particular structure of specimen cup system 10. Furthermore, there are several structural features shown in specimen cup system 10 that are present simply to facilitate the manufacture of system and, as such, are not limitations of the present invention. Where appropriate, the various manufacturing features of system 10 will be indicated.

Prior to describing specimen cup system 10 in detail, the basic parts of this embodiment are defined generally as follows:

a base 12, a sample cup 14 rotatably coupled to base 12, a test card support 16 coupled to sample cup 14, a test card cover 18 attachable to test card support 16, and a sample cup lid 20 attachable to an open top of sample cup 14.

Although not illustrated in FIG. 1, a specially-designed test card (that will fit in the combination of test card support 16 and test cover 18 as will be described later herein) can be included as part of the specimen cup system. The above terms will be used throughout the remainder of the description when referring to these parts of system 10.

Figure 3:
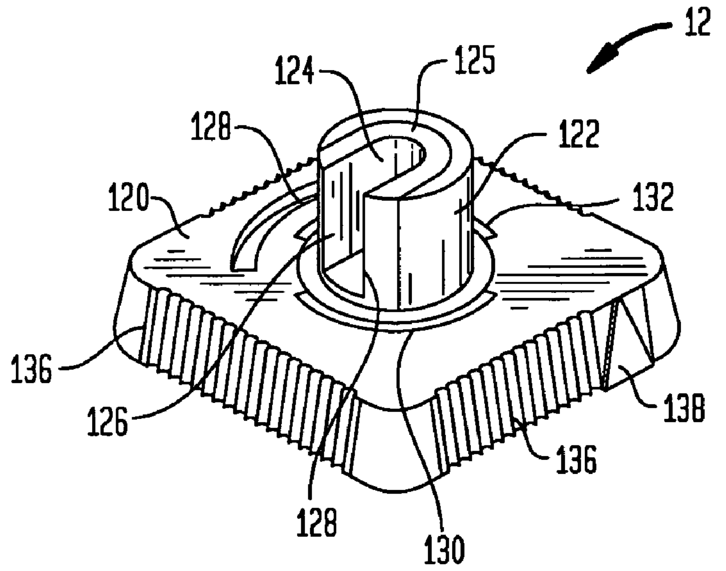
FIG. 3 is an isolated perspective view of the specimen cup system's base.
Figure 4:
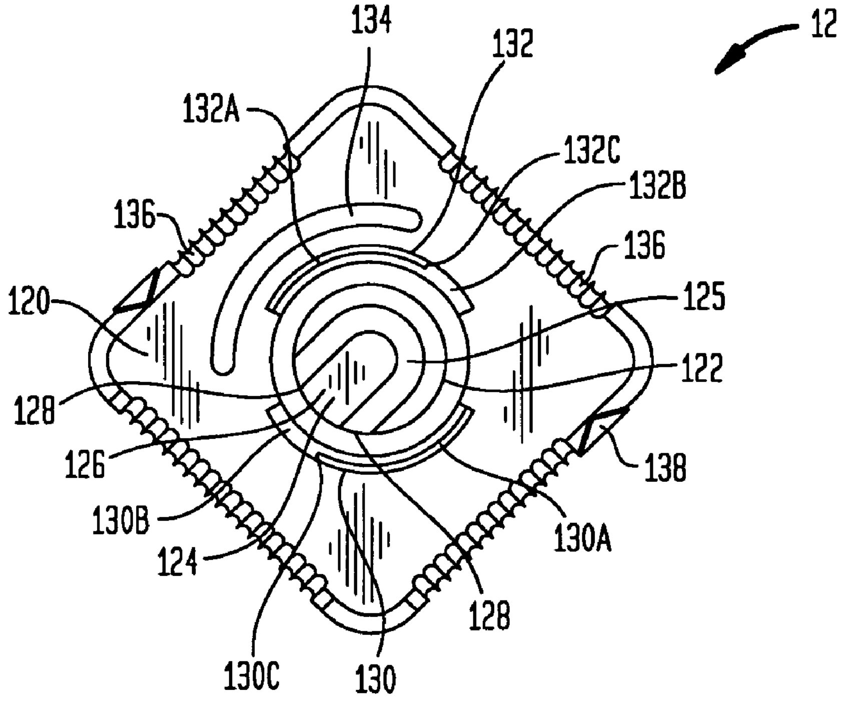
FIG. 4 is a top view of the base.
Figure 5:
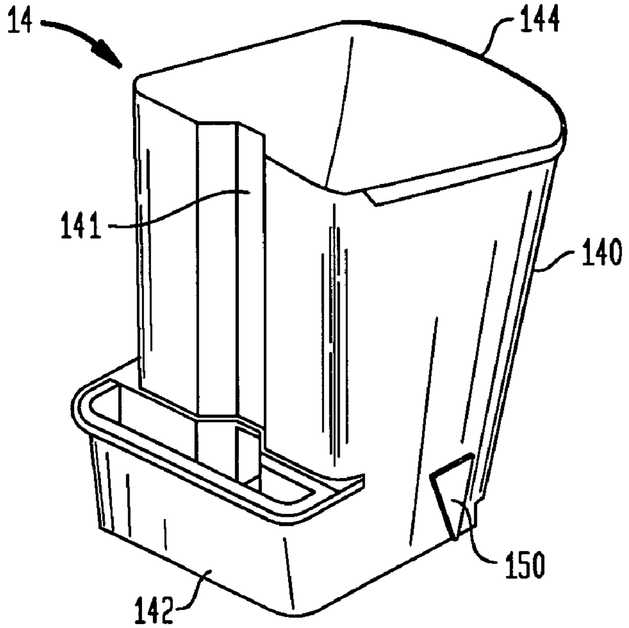
FIG. 5 is an isolated perspective view of an embodiment of the specimen cup system's sample cup.

Referring additionally now to FIGS. 3 and 4, base 12 will be described in greater detail. Base 12 has a support block 120 that can be sized/shaped to match the bottom of sample cup 14. Extending vertically upward from support block 120 is a hollow post 122. In the illustrated embodiment, support block 120 and post 122 are integrally formed (e.g., by injection molding). However, it is to be understood that the present invention is not so limited as other constructions could be utilized without departing from the scope of the present invention.

The hollow portion of post 122 defines a chamber 124 having a selected volume for the collection of a portion of a body-fluid sample as will be explained later below. Chamber 124 is accessed via an opening 126 in a radial wall of post 122. Opening 126 begins where post 122 and support block 120 meet and can extend up to the full height of post 122 as illustrated. The top of chamber 124 can be open (as shown) or closed without departing from the scope of the present invention. Opening 126 is framed by edges 128 that define a fluid-tight seal with the inside walls a post housing or receptacle (not shown) formed in sample cup 14 as will be described later below. Note that if the top of chamber 124 is open, the top edges 125 thereof must also define a fluid-tight seal with the inside top portion of the above-mentioned post receptacle.

Three curved slots are formed in support block 120. The first two slots 130 and 132 are typically cut all the way through support block 120 and are formed on diametrically-opposing sides of post 122 as best seen in FIG. 4. Each of slots 130 and 132 has a respective smaller width region 130A and 132A and a respective wider width region 130B and 132B such that respective lips 130C and 132C are formed at the interface of respective regions 130A/130B and 132A/132B. Wider width regions 130B and 132B essentially define notches that are diametrically-opposed to one another. The rotational angle defined by the length of slots 130 and 132 define the amount of rotational travel of base 12 relative to sample cup 14. For example, in the illustrated embodiment, the length of slots 130 and 132 will define approximately 90° of base rotation.

The third curved slot formed in support block 120 is a curved indexing 134 used to assure the proper positioning of base 12 relative to sample cup 14 during the assembly of base 12 to sample cup 14. Slot 134 can be cut partially into or all the way through support block 120. The rotational angle defined by the length of indexing slot 134 should be equal to or greater than that of slots 130 and 132.

To facilitate the gripping of base 12, some type of grip enhancement such as knurled edges 136 can be formed about some or all of the perimeter of support block 120. One or more positioning indicia 138 (e.g., marks, words, etc.) can also be provided (e.g., molded in, printed or painted on, attached to, etc.) on the perimeter of support block 120. Briefly, positioning indicia 138 are used to identify that specimen cup system 10 is in its pre-test or test position as will be described later below.

Referring additionally now to FIGS. 5-8, sample cup 14 will be described in greater detail. For clarity, sample cup 14 in FIGS. 5-8 is illustrated without base 12 coupled thereto. In general, sample cup 14 defines two open reservoirs or chambers 140 and 142 that, absent the presence of base 12, are in constant fluid communication with one another. However, when base 12 is rotatably attached to sample cup 14, fluid communication between chambers 140 and 142 is prohibited as will be explained further below. Chambers 140 and 142 defined by sample cup 14 are also referred to herein as a larger specimen cup 140 and a smaller test cup 142 formed adjacent the bottom of one side of specimen cup 140. In the illustrated embodiment, cups 140 and 142 are integrally formed during the manufacture of sample cup 14. However, it is to be understood that the present invention is not so limited as other constructions of sample cup 14 are possible without departing from the scope of the present invention. Test cup 142 will typically be made from a transparent material to clearly indicate the presence of a body-fluid sample and the position of the lower portion of a test card (not shown) that will be fitted partially in test cup 142 as will be explained further below.

Figure 6:
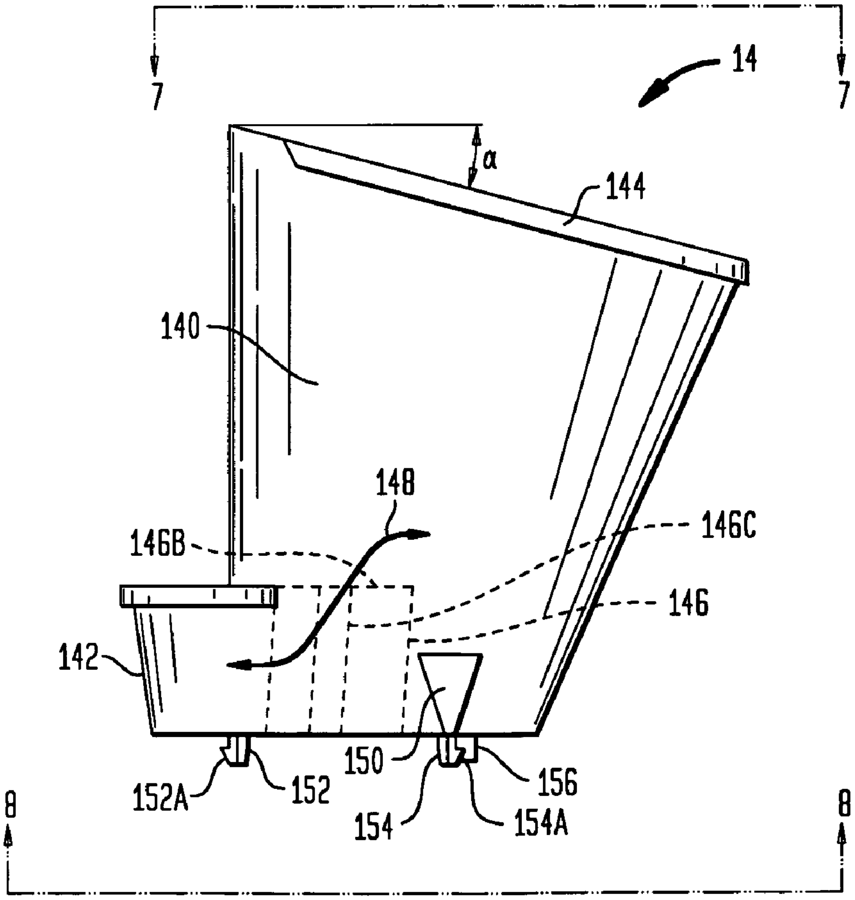
FIG. 6 is a side view of the sample cup.
Figure 7:
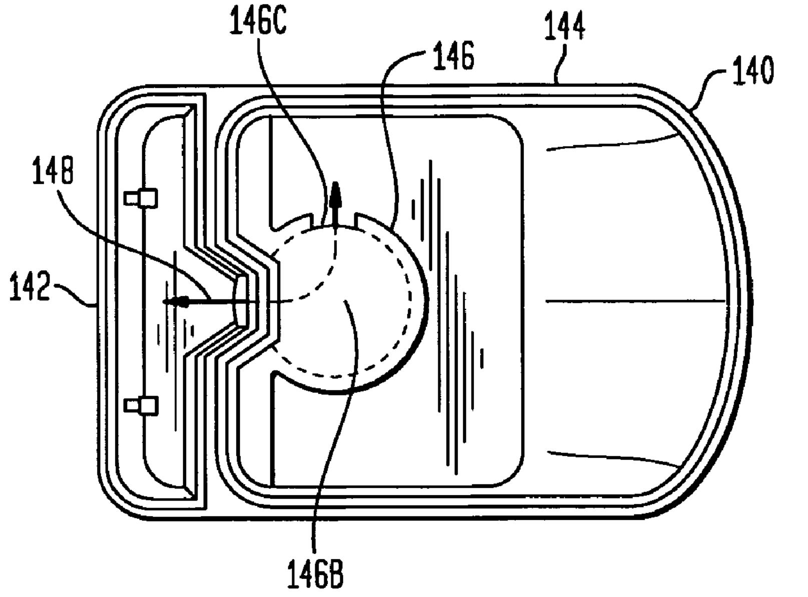
FIG. 7 is a top view of the sample cup taken along line 7-7 in FIG. 6.

Specimen cup 140 is open at the top thereof where a lip 144 is formed at least partially therearound. Lip 144 is designed such that lid 20 (FIGS. 1 and 2) seals and locks onto cup 140 in a secure tamper-resistant fashion. The particular design of lip 144 and the mating portions of lid 20 are not limitations of the present invention. The top of specimen cup 140 is pitched downward at an angle $\alpha$ as best seen in FIG. 6 to facilitate the filling thereof with urine by a female user. Angle $\alpha$ can range from approximately 10° to approximately 20° with approximately 15° being typical.

Formed on the inside of specimen cup 140 at the bottom thereof is a hollow post housing or receptacle 146 having an open bottom 146A (FIG. 8), a closed top 146B (FIG. 7), and first and second openings 146C and 146D formed in radial sides thereof. First opening 146C defines an opening between specimen cup 140 and the interior of post receptacle 146. Second opening 146D defines an opening between test cup 142 and the interior of post receptacle 146. The angular spacing between openings 146C and 146D matches the rotation angle defined by slots 130 and 132 in base 12 as described above. Thus, in the illustrated example, openings 146C and 146D are angularly spaced by approximately 90°. Openings 146C and 146D should be defined at least at the lower portion of post receptacle 146 and can extend for the full height of post receptacle 146 as illustrated. Without base 12 coupled to specimen cup 140, the interior of specimen cup 140 is in fluid communication with the interior of test cup 142 via post receptacle 146 and openings 146C/146D formed therein. This fluid communication is indicated in the various views by two-headed arrow 148.

Test cup 142 is open at the top thereof and is shaped (e.g., substantially rectangular as illustrated) to accommodate a flat test card (not shown). As shown in FIG. 1, test card support 16 will be fitted in and fixed to (e.g., fused, glued, sealed, etc.) the top of test cup 142. It is to be understood that while test card support 16 is a separate element in the illustrated embodiment, the separate nature thereof is merely to facilitate the manufacturing of specimen cup system 10. That is, the test card support features provided by test card support 16 could be integrated with sample cup 14 without departing from the scope of the present invention. In addition, it is to be understood that the vertical indentation 141 formed in specimen cup 140 and test cup 142 is there simply to facilitate the manufacturing of sample cup 14 and is not a required feature of the present invention.

Provided on the lower outside portion of specimen cup 140 is one or more positioning indicia 150. The relative positions of positioning indicia 138 provided on base 12 and positioning indicia 150 are used to identify when specimen cup system 10 is in its pre-test or test position. For example, the relative positions of indicia 138 and 150 shown in FIG. 1 could indicate a pre-test position of system 10. Positioning indicia 150 can be molded into specimen cup 140, or applied thereto by any of a variety of methods.

Figure 8:
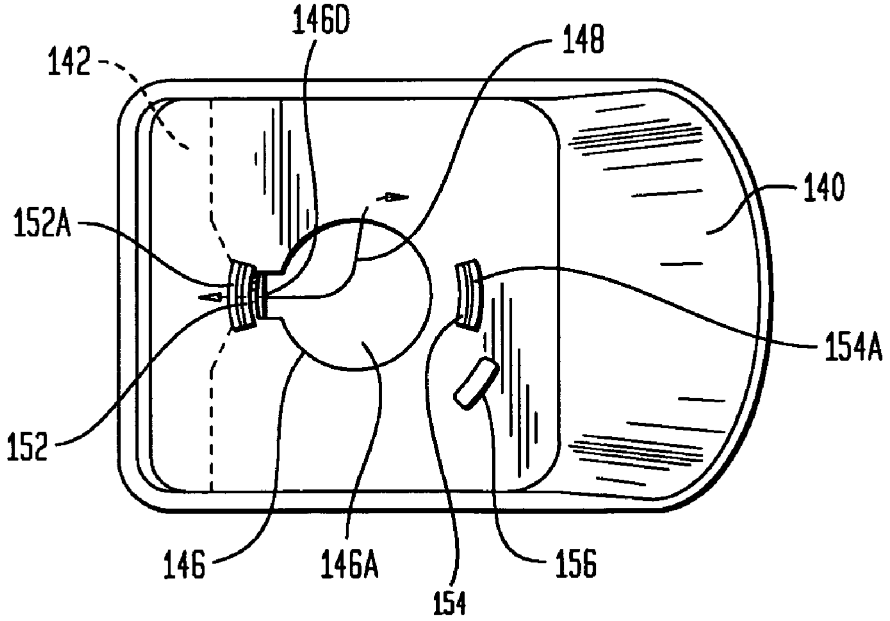
FIG. 8 is a bottom view of the sample cup taken along line 8-8 in FIG. 6.

Affixed to (or integral with) and extending downward from the bottom of specimen cup 140 are three tabs 152, 154, and 156. Tabs 152 and 154 are diametrically disposed about the open bottom 146A of post receptacle 146 as best seen in FIG. 8. Each of tabs 152 and 154 has a lip 152A and 154A, respectively, formed at the outboard ends thereof. Tabs 152 and 154 are biased away from one another. To understand the assembly of base 12 to sample cup 14, simultaneous reference will be made to FIGS. 4, 6 and 8. When base 12 is assembled to the bottom of sample cup 14, tabs 152 and 154 respectively engage slots 130 and 132 of base 12. The outward bias of tabs 152 and 154 allows lips 152A and 154A, respectively, to lock onto the underside of support block 120 after tabs 152 and 154 have been pushed through slots 130 and 132. The outward bias of tabs 152 and 154 also allows the tabs to spring radially outward into respective wider width regions 130B and 132B when the tabs are aligned therewith. Once tabs 152 and 154 are engaged in these wider width regions, respective lips 130C and 132C lock tabs 152 and 154 in that portion of slots 130 and 132. Tab 156 is an indexing tab that will engage indexing slot 134 when base 12 is assembled to the bottom of sample cup 14. Note that the present invention could also be practiced by configuring sample cup 14 with the above-described arrangement of slots and configuring base 12 with the corresponding arrangement of tabs.

Figure 9:
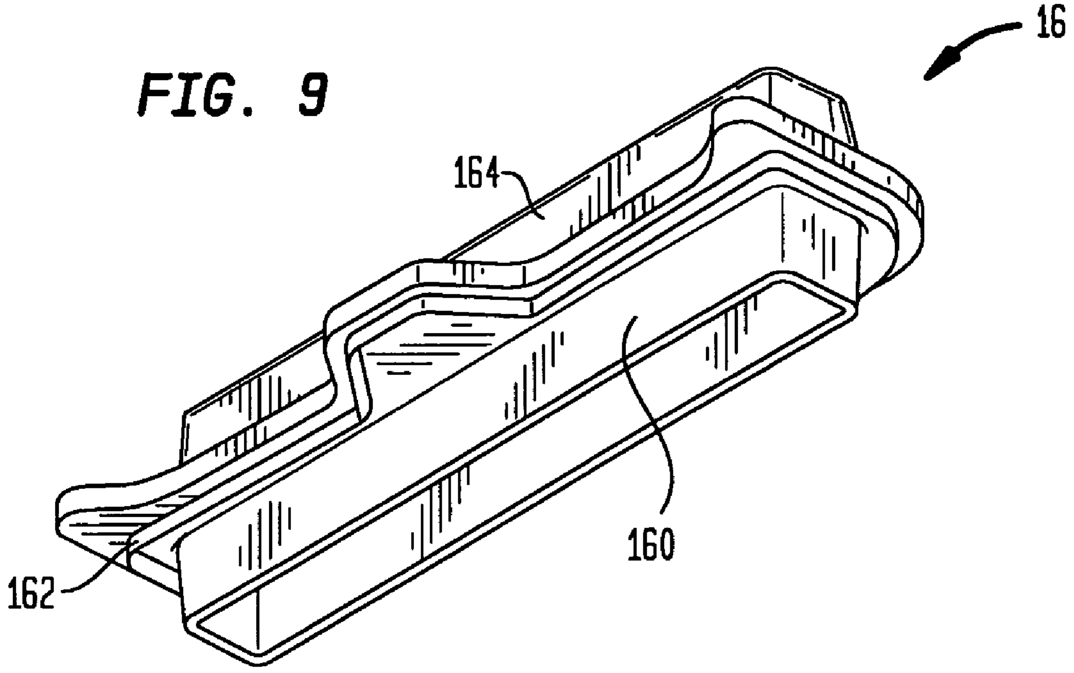
FIG. 9 is an isolated and underside perspective view of the specimen cup system's test card support in accordance with the system embodiment illustrated in FIG. 1.
Figure 10:
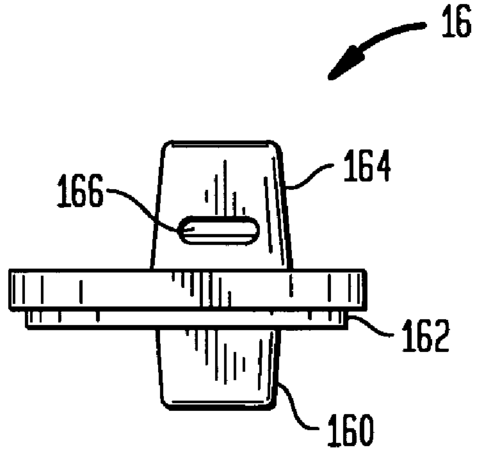
FIG. 10 is a side view of the test card support.
Figure 11:
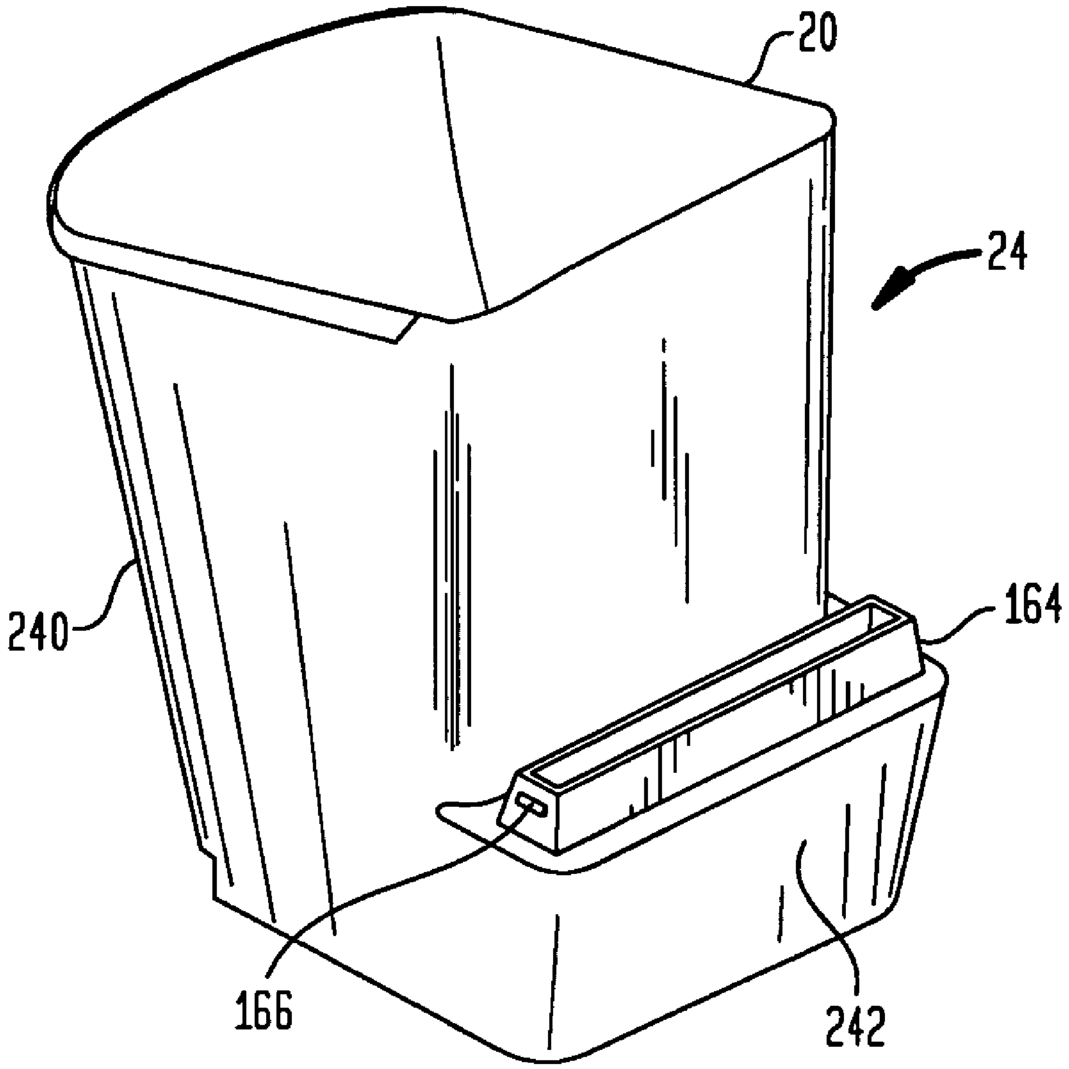
FIG. 11 is an isolated perspective view of another embodiment of the specimen cup system's sample cup.

Referring additionally now to FIGS. 9 and 10, test card support 16 will be described in greater detail. As mentioned above, the separate nature of test card support 16 is merely to facilitate manufacture of the illustrated embodiment. Accordingly, it is to be understood that the features of test card support 16 could be integrated directly into sample cup 14 (as illustrated in FIG. 11) without departing from the scope of the present invention. In general, test card support 16 is a sleeve that fits partially into test cup 142 and then is affixed thereto in a sealed fashion in any of a variety of ways known in the art. Once in place, test card support 16 can securely position a test card (not shown) with the test regions thereof disposed at the correct position in test cup 142 as will be explained below.

Test card support 16 is defined by a lower sleeve 160, an annular seating flange 162, and an upper sleeve 164. Lower sleeve 160 fits into the top of test cup 142 and annular flange 162 sits/fits on the top of test cup 142. The shape of annular seating flange 162 accommodates the shape of the top of test cup 142, but the particular shape is not a limitation of the present invention. When annular seating flange 162 rests on and is sealed to the top of test cup 142, upper sleeve 164 extends from the top of test cup 142. A rib 166 protrudes from opposing short sides of upper sleeve 164. Rib 166 will mate with a complimentary notch formed on the inside of test card cover 18 as will be explained below. In this way, cover 18 can be locked onto upper sleeve 164.

As mentioned above, sample cup 14 and test card support 16 could be constructed as a one-piece integrated part without departing from the scope of the present invention. Accordingly, FIG. 11 illustrates a sample cup 24 that integrates the previously-described sample cup 14 and test card support 16 into a one-piece design. In general, sample cup 24 defines a specimen cup 240 and a test cup 242 having the above-described upper sleeve 164 and rib 166 integrated therewith. Furthermore, while not all of the features are visible in FIG. 11, it is to be understood that sample cup 24 also has the various novel features (e.g., post receptacle 146, tabs 152/154/156, etc.) described in detail above with respect to sample cup 14.

Figure 12:
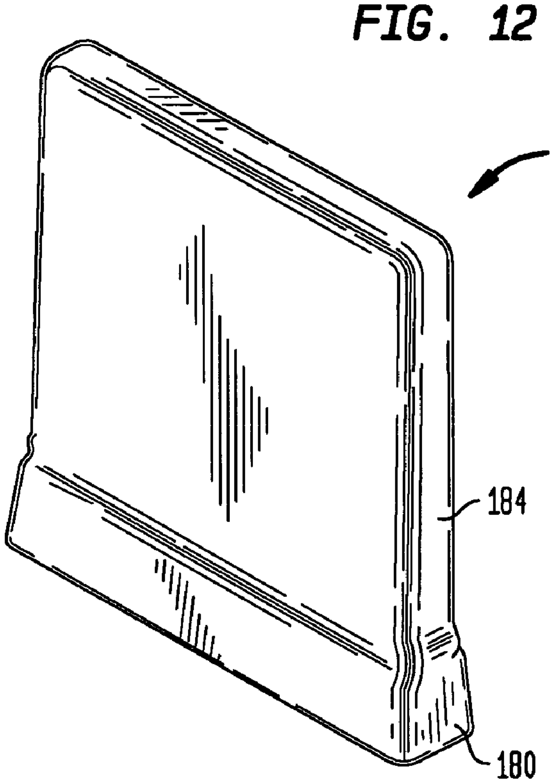
FIG. 12 is an isolated perspective view of an embodiment of the specimen cup system's test card cover.
Figure 13:
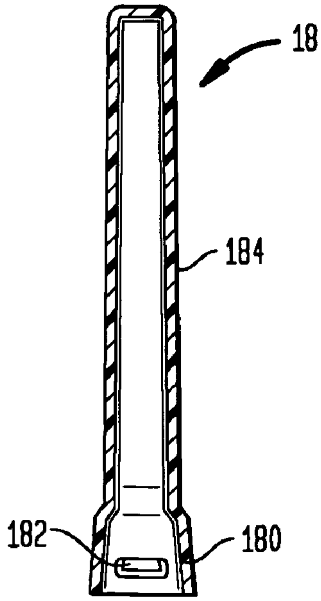
FIG. 13 is a cross-sectional view of the test card cover.

Referring additionally now to FIGS. 12 and 13, test card cover 18 will be described in greater detail. Cover 18 will typically be made from a transparent material to facilitate the reading of a test card (not shown) positioned therein as will be explained further below. Cover 18 includes an open base 180 designed to fit over upper sleeve 164 protruding up from test cup 142. Base 180 defines two interior notches 182 (one of which is visible in FIG. 13) that will engage and lock onto ribs 166 formed on the outside of upper sleeve 164. Extending up from base 180 is an enclosed region 184 that will house the test strip portion of a test card (not shown). The flat surface defined by the front face of test cup 142 and test card cover 18 will simplify the placement of specimen cup system 10 on a copy machine to record the results indicated by a test card housed therein.

Figure 14:
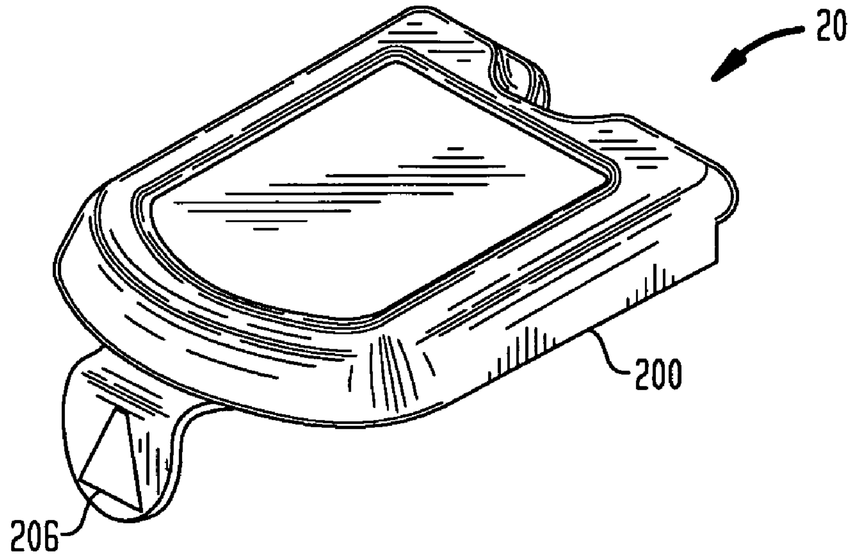
FIG. 14 is an isolated perspective view of an embodiment of the specimen cup system's sample cup lid.
Figure 15:
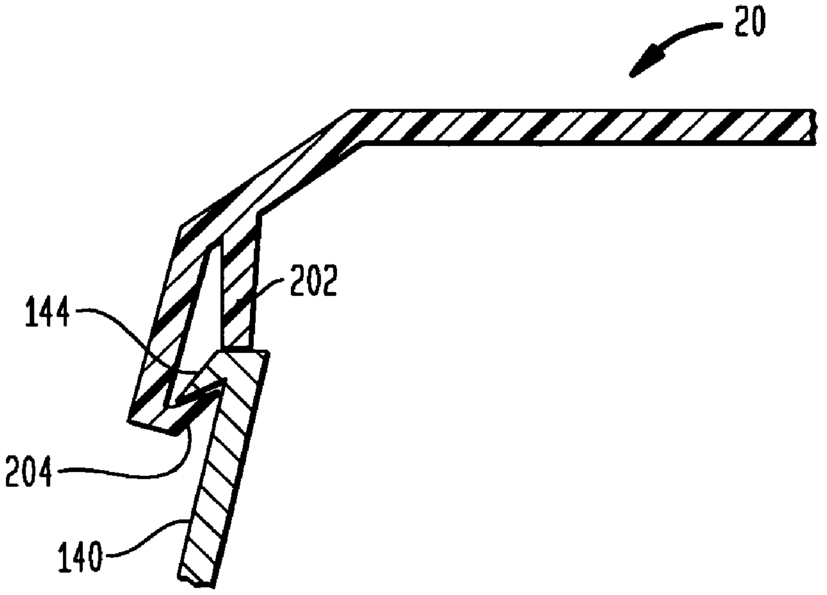
FIG. 15 is an isolated cross-sectional view of an embodiment of the locking portion of the sample cup lid.

Referring additionally now to FIGS. 14 and 15, sample cup lid 20 will be explained in greater detail. In general, lid 20 is configured to form a sealed and locked fit with the top of sample cup 140. Lid 20 can be configured such that it can be removed without damage thereto. However, the present invention is not so limited as lid 20 can also be configured such that removal of lid 20 can only be achieved by the breakage thereof thereby clearly indicating tampering.

As illustrated, sample cup lid 20 is configured to cooperate with the top of sample cup 14 illustrated in FIG. 1. However, it is to be understood that sample cup lid 20 could also be configured to cooperate with the top of sample cup 24 illustrated in FIG. 11. Furthermore, it is to be understood that a variety of designs are possible for both the top of sample cup 140 and the periphery 200 of lid 20 without departing from the scope of the present invention. For example, in the illustrated embodiment, the portion of lid 20 that will engage lip 144 of sample cup 140 can be constructed as shown in FIG. 15 where lip 144 will be captured between ribs 202 and 204 formed about the portion of periphery 200 that will mate with lip 144. If any portions of the top of sample cup 140 do not incorporate a lip, the complementary portion of periphery 200 can simply define a channel that engages and seals to sample cup 140 as would be understood in the art. A removal tab 206 is provided on lid 20 to facilitate removal of lid 20 after it has been installed on sample cup 140. Removal tab 206 essentially acts as a "pry bar" that pries rib 202 off of lip 144. In doing this, lid 20 cracks, displays regions of stress, or breaks thereby providing evidence of tampering.

Figure 16:
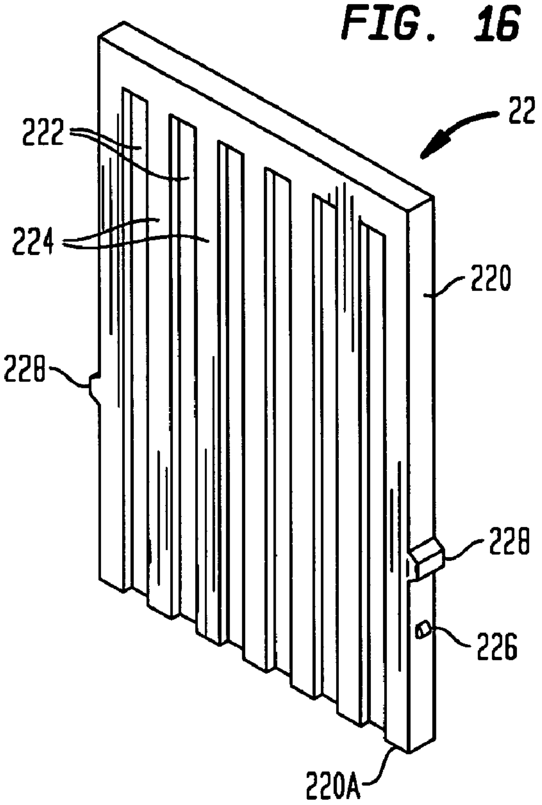
FIG. 16 is a perspective view of an embodiment of a test card that can be included in the specimen cup system.
Figure 17:
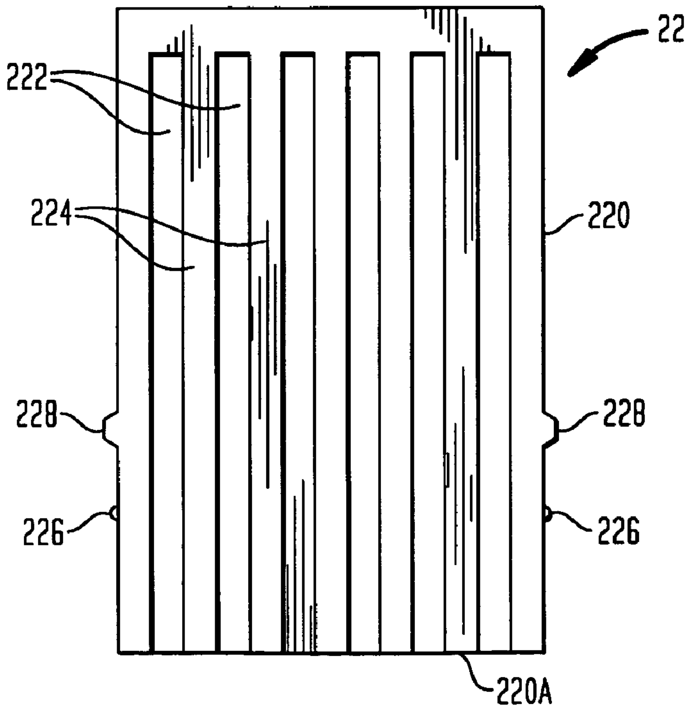
FIG. 17 is a front, plan view of the test card.

As mentioned above, the test card used in specimen cup system can be included as part of the present invention, or the present invention could be used with other commercially-available test cards. If part of the present invention, the test card can be configured as shown in FIGS. 16 and 17. More specifically, a test card 22 has a rectangular body 220 that defines a plurality of vertical channels 222 that will have a chemical test strip (not shown) fitted therein. Such test strips are well known in the art and will not be described further herein. The long regions 224 between channels 222 will typically have indicia (not shown) placed thereon to indicate the particular test being indicated by the test strip in a channel. Disposed on either side of body 220 are securing ribs 226 that engage the inside walls of upper sleeve 164/test cup 142 to prevent test card 22 from wobbling therein. Disposed on either side of body 220 and above securing ribs 226 are travel stops 228 that will engage the top of upper sleeve 164 when test card 22 is placed therein. The position of travel stops 228 is selected such that the bottom 220A of body 220 will reside just above the bottom of test cup 142.

In describing the operation of the present invention, reference will be made to all of the above-described views of the present invention. Prior to use of the specimen cup system of the present invention, base 12 is coupled to sample cup 14 (or sample cup 24) using the above-described tab-to-slot matings. In its pre-test position, opening 126 in post 122 (of base 12) is aligned with first opening 146C of post receptacle 146 (of sample cup 14). In this way, chamber 124 in post 122 is in fluid communication with specimen cup 140 while being sealed off from test cup 142. When a body-fluid sample is deposited in specimen cup 140, chamber 124 fills with a portion of the body-fluid sample. Lid 20 is then installed on and sealed to sample cup 140 as described above. If desired, a security tape (not shown) can be applied to/over lid 20 as is known in the art.

At test time, test card 22 (or other test card) is placed in upper sleeve 164 and test card cover 18 is placed over test card 22 and locked in place via engagement of ribs 166 and notches 182 as described above. To perform the test, base 12 is simply rotated until opening 126 in post 122 is aligned with second opening 146D of post receptacle 146. Once openings 126 and 146D are aligned, the portion of the body-fluid sample in chamber 124 flows via gravity into test cup 142 where it can come into contact with the test strips in test card 22. Note that during the rotation of base 12, edges 128 of opening 126 (and, if present, edges 125) seal against the inside walls of post receptacle 146 to thereby seal off specimen cup 140 and maintain any remaining body-fluid sample in sample cup 140 in a contaminant-free state. Such rotation of base 12 will also place positioning indicia 138 and 150 in positions (e.g., on the same side of specimen cup system 10, aligned with one another, etc.) that clearly indicate that specimen cup system 10 is in its test position.

Once openings 126 and 146D are aligned, tabs 152 and 154 will reside in the wider width regions or notches 130B and 132B of slots 130 and 132 (in base 12). The bias in tabs 152 and 154 causes them to flex radially outward such that tabs 152 and 154 are captured in wider width regions 130B and 132B, respectively. That is, any attempt to rotate base 12 back to its pre-test position would cause tabs 152 and 154 to engage the corresponding lips 130C and 132C of slots 130 and 132. In this way, base 12 is locked in the test position and is prevented from rotation back to the system's pre-test position (i.e., where opening 126 is aligned with opening 146C). With base 12 locked in the test position, the remaining portion of the body-fluid sample in specimen cup 140 cannot be accessed unless lid 20 is removed/broken as described above. As a result, once specimen cup system 10 has been placed in the test position, the remaining body-fluid sample in sample cup 140 is guaranteed to be contaminant-free provided lid 20 is not removed/broken. Accordingly, the present invention guarantees the trustworthiness of any follow-up testing on the remaining body-fluid sample.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A specimen cup system for sample testing, comprising:
- a cup defining a first region and a second region adjacent to said first region;
- a receptacle formed at a bottom of said first region and extending vertically therein, said receptacle having (i) a first opening defined at said bottom of said first region, (ii) a second opening in a radial wall of said receptacle for fluid communication with said first region, and (iii) a third opening in said radial wall of said receptacle for fluid communication with said second region;
- a base having a hollow post extending vertically therefrom for insertion in said first opening of said receptacle, said hollow post having a radial opening formed therein that, when aligned with said second opening, defines a pre-test condition, said hollow post forming a fluid tight seal with said receptacle about said radial opening;
- means for coupling said base to said bottom of said cup in a rotatable fashion wherein said hollow post can be rotated to align said radial opening with said third opening to define a test condition, said means for coupling further locking said base to said cup when said test condition is so-defined;
- a first top for sealing said first region; and
- a second top for sealing said second region.

2. A specimen cup system as in claim 1, further comprising first indicia on said cup and second indicia on said base wherein one of said pre-test condition and said test condition are indicated by a location of said first indicia relative to a location of said second indicia.

3. A specimen cup system as in claim 1, wherein said second region is adapted to receive a portion of a specimen test card therein, and wherein said second top is adapted to encase a remaining portion of the specimen test card extending from said second region.

4. A specimen cup system as in claim 1, further comprising a specimen test card for partial insertion in said second region, said specimen test card having at least one stop formed thereon for engaging said second region to define said partial insertion.

5. A specimen cup system as in claim 1, wherein said means for coupling comprises:
- an arrangement of tabs coupled to and extending from said bottom of said first region; and
- an arrangement of slots formed in said base in correspondence with said arrangement of tabs for engagement therewith.

6. A specimen cup system as in claim 5, wherein two of said tabs are disposed about said first opening at diametrically opposed locations, said two of said tabs being biased away from one another.

7. A specimen cup system as in claim 1 wherein, when said base is coupled to said bottom of said cup and said base is adapted to rest on a planar surface, a top of said first region defines a plane that is non-parallel with respect to the planar surface.

8. A specimen cup system for sample testing, comprising:

a cup defining a first open reservoir and a second open reservoir adjacent to said first open reservoir;

a cylindrical receptacle formed at a bottom of said first region and extending vertically therein, said receptacle having (i) a first opening defined at said bottom of said first open reservoir, (ii) a second opening in a radial wall of said receptacle for fluid communication with said first open reservoir, and (iii) a third opening in said radial wall of said receptacle for fluid communication with said second open reservoir;

a base having a hollow post extending vertically therefrom for insertion in said first opening of said receptacle, said hollow post having a radial opening formed therein that, when aligned with said second opening, defines a pre-test condition, said hollow post forming a fluid tight seal with said receptacle about said radial opening;

an arrangement of tabs coupled to and extending from said bottom of said first region;

an arrangement of slots formed in said base in correspondence with said arrangement of tabs, wherein said base is coupled to said bottom of said cup in a rotatable fashion by engagement of said tabs with said slots and wherein said hollow post can be rotated to align said radial opening with said third opening to define a test condition;

a first top for sealing said first open reservoir; and a second top for sealing said second open reservoir.

9. A specimen cup system as in claim 8, further comprising first indicia on said cup and second indicia on said base wherein one of said pre-test condition and said test condition are indicated by a location of said first indicia relative to a location of said second indicia.

10. A specimen cup system as in claim 8, wherein said second open reservoir is adapted to receive a portion of a specimen test card therein, and wherein said second top is adapted to encase a remaining portion of the specimen test card extending from said second open reservoir.

11. A specimen cup system as in claim 8, further comprising a specimen test card for partial insertion in said second open reservoir wherein said specimen test card extends therefrom, said specimen test card having at least one stop formed thereon for engaging said second open reservoir to define said partial insertion, and wherein said second top encases portions of said specimen test card extending from said second open reservoir.

12. A specimen cup system as in claim 8, wherein two of said tabs are lipped tabs disposed about said first opening at diametrically opposed locations, said lipped tabs being biased away from one another.

13. A specimen cup system as in claim 12, wherein each of said slots engaging said lipped tabs is configured to prevent further rotation of said hollow post once said test condition is so-defined.

14. A specimen cup system as in claim 8 wherein, when said base is coupled to said bottom of said cup and said base is adapted to rest on a planar surface, a top of said first open reservoir defines a plane that is non-parallel with respect to the planar surface.

15. A specimen cup system for sample testing, comprising:

a cup defining a first region and a second region adjacent to said first region;

a receptacle formed at a bottom of said first region and extending vertically therein, said receptacle having (i) a first opening defined at said bottom of said first region, (ii) a second opening in a radial wall of said receptacle for fluid communication with said first region, and (iii) a third opening in said radial wall of said receptacle for fluid communication with said second region;

a base having a hollow post extending vertically therefrom for insertion in said first opening of said receptacle, said hollow post having a radial opening formed therein that, when aligned with said second opening, defines a pre-test condition, said hollow post forming a fluid tight seal with said receptacle about said radial opening;

means for coupling said base to said bottom of said cup in a rotatable fashion wherein said hollow post can be rotated to align said radial opening with said third opening to define a test condition, said means for coupling further locking said base to said cup when said test condition is so-defined;

a first cover for sealing said first region;

first indicia on said cup;

second indicia on said base wherein one of said pre-test condition and said test condition are indicated by a location of said first indicia relative to a location of said second indicia;

a specimen test card for partial insertion in said second region, said specimen test card having at least one stop formed thereon for engaging said second region to define said partial insertion; and a second cover for sealing said second region with portions of said specimen test card protruding from said second region being encased thereby.

16. A specimen cup system as in claim 15, wherein said means for coupling comprises:

an arrangement of tabs coupled to and extending from said bottom of said first region; and an arrangement of slots formed in said base in correspondence with said arrangement of tabs for engagement therewith.

17. A specimen cup system as in claim 16, wherein two of said tabs are disposed about said first opening at diametrically opposed locations, said two of said tabs being biased away from one another.

18. A specimen cup system as in claim 17, wherein said two of said tabs are lipped tabs disposed about said first opening at diametrically opposed locations, said lipped tabs being biased away from one another.

19. A specimen cup system as in claim 18, wherein each of said slots engaging said lipped tabs include a notched region for capturing one of said lipped tabs to prevent further rotation of said hollow post once said test condition is so-defined.

20. A specimen cup system as in claim 15 wherein, when said base is coupled to said bottom of said cup and said base is adapted to rest on a planar surface, a top of said first region defines a plane that is non-parallel with respect to the planar surface.

* * * * *

UNITED STATES PATENT AND TRADEMARK OFFICE

CERTIFICATE OF CORRECTION

PATENT NO. : 7,927,560 B2
APPLICATION NO. : 12/381722
DATED : April 19, 2011
INVENTOR(S) : Richard M. Nee It is certified that error appears in the above-identified patent and that said Letters Patent is hereby corrected as shown below:

On the title page, item (12) of the patent, the inventor's last name should be "Nee" in the upper left hand corner underneath the words "United States Patent".

On the title page, item (75) of the patent, the inventor's full name appearing after "Inventor" in the left hand column should be "Richard M. Nee".

Signed and Sealed this
Seventh Day of June, 2011

David J. Kappos
*Director of the United States Patent and Trademark Office*